United States Patent [19]

Roques et al.

[11] 4,407,794

[45] Oct. 4, 1983

[54] PEPTIDES AND THERAPEUTIC APPLICATIONS THEREOF

[75] Inventors: Bernard Roques, Saint Maurice; Jeanne-Marie Lecomte, Paris, both of France

[73] Assignee: Centre National de la Recherche Scientifique (CNRS), Paris, France

[21] Appl. No.: 289,383

[22] Filed: Aug. 3, 1981

[30] Foreign Application Priority Data

Aug. 8, 1980 [FR] France ............................ 80 17523

[51] Int. Cl.³ .................... A61K 37/00; C07C 103/52
[52] U.S. Cl. ............................ 424/177; 260/112.5 E
[58] Field of Search ................ 260/112.5 E; 424/177

[56] References Cited

U.S. PATENT DOCUMENTS

| | | | |
|---|---|---|---|
| 4,162,307 | 7/1979 | Wilkinson | 260/112.5 E |
| 4,196,122 | 4/1980 | Sarantakis | 260/112.5 E |
| 4,213,968 | 7/1980 | Kastin et al. | 260/112.5 E |
| 4,216,127 | 8/1980 | Sarantakis | 260/112.5 E |
| 4,247,543 | 1/1981 | Pless et al. | 260/112.5 E |
| 4,259,234 | 3/1981 | Smithwick, Jr. et al. | 260/112.5 E |
| 4,261,888 | 4/1981 | Bauer et al. | 260/112.5 E |
| 4,264,491 | 4/1981 | Smithwick, Jr. et al. | 260/112.5 E |
| 4,278,596 | 7/1981 | Garsky | 260/112.5 E |
| 4,283,329 | 8/1981 | Gesellchen et al. | 260/112.5 E |
| 4,309,343 | 1/1982 | Gesellchen | 260/112.5 E |
| 4,322,339 | 3/1982 | Gesellchen et al. | 260/112.5 E |
| 4,322,342 | 3/1982 | Smithwick, Jr. et al. | 260/112.5 E |
| 4,331,593 | 5/1982 | Smithwick, Jr. et al. | 260/112.5 E |

FOREIGN PATENT DOCUMENTS 2703109 4/1977 Fed. Rep. of Germany ... 260/112.5 R

*Primary Examiner*—Delbert R. Phillips
*Attorney, Agent, or Firm*—Young & Thompson

[57] ABSTRACT

This invention relates to peptide derivatives of the formula:

Tyr—A—Gly—B—C—D    (I)

in which:

A is a D.Ala, AzaGly, Aib, D.Ser., D.Thr, D.Cys, homo Serine, βPhe Ser, βOH Leu, 4OH Ile, α,β,γ OHNor Val or OH Val residue in which the side-chain OH or SH groups, when same exist, may be free or protected (i) by a straight- or branched-chain alkyl containing 1-6 carbon atoms, (ii) by an unsubstituted phenyl radical or a phenyl radical substituted with one or more fluorine atoms, (iii) by an unsubstituted benzyl radical or a benzyl radical substituted with one or more fluorine atoms, (iv) by an aliphatic acyl radical having 1-6 carbon atoms or an acyl radical COX in which X is a phenyl, benzyl or benzhydryl radical, optionally substituted with one or more fluorine atoms, B is a L.Phe, pF.L.Phe or pentafluoro L.Phe residue, C is a Leu, N.Leu or Ile residue of D or L configuration, D is hydrogen or a group of the formula:

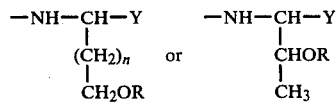

in which n=0, 1 or 2,

R is a hydrogen atom or a radical as defined for the protection of group OH of residue A, Y is a hydrogen atom, a group hydroxy, carboxy, carbamoyl, a group $OR_1$, $COOR_1$ or $CONHR_1$ in which $R_1$ represents a radical as defined for the protection of group OH of residue A, a phosphatidylethanolamine chain or a chain

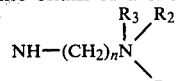

in which n is an integer from 0 to 3, $R_2$ is a hydrogen atom or a straight alkyl radical containing 1-4 carbon atoms, and $R_3$ is a hydrogen or oxygen atom or a straight alkyl residue containing 1-4 carbon atoms, and their pharmaceutically acceptable salts.

Said compounds are therapeutically useful, typically an analgesic, psychotropic and anti-diarrheic agents.

5 Claims, No Drawings

PEPTIDES AND THERAPEUTIC APPLICATIONS THEREOF

This invention relates to new peptides which possess a substantial activity on δ opiate receptors, and to their therapeutic applications, typically as analgesic and psychotropic agents.

This invention concerns more particularly penta-and hexa-peptides having a substantial activity on δ opiate receptors.

Pentapeptides exhibiting some structural analogy have already been disclosed in patent FR 78 12 543. However, said known compounds have practically no activity on δ opiate receptors.

It is known that there exist at least two types of opiate receptors (μ and δ) in the brain (KOSTERLITZ et al. (1980), Brit. J. Pharmacol., 68, 333-42, CHANG et al. (1979), J. Biol. Chem., 254, 2610-18).

Both these types of receptors are involved in analgesy, but the δ receptors also appear to be involved in behavior, emotional conditions, etc.. (RICHTER et al. (1980) Life Sciences 26, 337-42).

The materials which exhibit a specific activity on δ receptors ordinarily have habit-forming and dependence effects greatly inferior to those generated by conventional opiates (morphine, pethidine) or by the presently disclosed enkephalin derivatives (Frederickson et al. Science, 211, 603-605 (1981).

Thus, the object of this invention is to provide compounds having a substantial specific activity on a single type of receptors, i.e. δ receptors.

This invention relates to peptide derivatives having the general formula:

Tyr—A—Gly—B—C—D    (I)

in which:

A is a D.Ala, AzaGly, Aib, D.Ser, D.Thr, D.Cys, homo Serine, βPhe Ser, βOH Leu, 4OH Ile, α,β,γ OHNor Val or OH Val residue in which the side-chain OH or SH groups, when same exist, may be free or protected by (i) a straight- or branched-chain alkyl radical having 1-6 carbon atoms, (ii) by an unsubstituted phenyl radical or a phenyl radical substituted with one or more fluorine atoms, (iii) by an unsubstituted benzyl radical or a benzyl radical substituted with one or more fluorine atoms, (iv) by an aliphatic acyl radical having 1-6 carbon atoms or by an acyl radical of the formula COX in which X is a phenyl, benzyl or benzhydryl radical, optionally substituted with one or more fluorine atoms, B is a L.Phe, pF.L.Phe or pentafluoro L.Phe residue, C is a Leu, N.Leu or Ile residue having D or L configuration, D represents a hydrogen atom or a group of the formula:

in which n=0, 1 or 2,

R is a hydrogen atom or a radical as defined for the protection of the OH group of residue A, Y is a hydrogen atom, a hydroxy, carboxy, carbamoyl oxy group, a group $OR_1$, $COOR_1$ or $CONHR_1$ in which $R_1$ represents a radical such as defined for the protection of the OH group of residue A, a phosphatidylethanolamine chain, or a chain

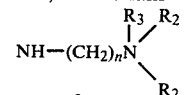

in which n is an integer from 0 to 3, $R_2$ is a hydrogen atom or a straight alkyl radical containing 1-4 carbon atoms, and $R_3$ is a hydrogen or oxygen atom or a straight alkyl residue having 1-4 carbon atoms and their pharmaceutically acceptable salts.

The compounds of the formula (I) may be prepared according to the conventional methods for peptide synthesis. Thus, they may be obtained by fragmentary condensation or by series coupling of suitably selected and protected aminoacids. The coupling reaction is effected according to the usual activation methods and the deprotection methods conventionally used in peptide synthesis.

Details concerning such conventional methods may be found in the following references:

1. C. GARBAY-JAUREGUIBERRY, B. P. ROQUES, R. OBERLIN, M. ANTEUNIS & A. K. LALA B.B.R.C., 71, 558-565, 1976.
2. C. GARBAY-JAUREGUIBERRY, B. P. ROQUES, R. OBERLIN, M. ANTEUNIS, S. COMBRISSON & J. Y. LALLEMAND FEBS Letters, 76, 93-98, 1977.
3. J. D. BOWER et al., J. Chem. Soc. Perkin Trans I, 2488-92.
4. W. WOELTER et al., Angen. Chem., Int. Ed. Engl., 15, 297(1976).
5. E. PIETRZIK et al., Liebigs Ann. Chem. p. 609 (1977)

As a general example, the compounds of the formula (I) may be prepared by condensation of a M Tyr-OH residue in which M represents a protecting group for the amino function (tert.butyloxycarbonyl, benzyloxycarbonyl, fluorenylmethyloxycarbonyl) with a H-A-P residue in which P is a protecting group for the acid function (e.g., ester). The combination is effected by use of conventional promoters, and more particularly of dicyclohexylcarbodiimide and hydroxybenzotriazole.

Selective removal of protecting group E makes it possible to continue the synthesis by successive condensation, until the desired peptide is obtained.

In the case of fragment-wise synthesis, the methods used are similar, but sets of residues are then coupled according to the scheme:

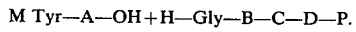

The following non-limiting Examples illustrate the present invention. In said Examples, the following abbreviations are used:

BOC=tert.butyloxycarbonyl
t.bu=tert.butyl
DCC=dicyclohexylcarbodiimide
HOBT=hydroxybenzotriazole
Z=benzyloxycarbonyl
DCU=dicyclohexylurea
AcOEt=ethyl acetate
THF=tetrahydrofuran
NEt₃=triethylamine
TFA=trifluoroacetic acid.

The various compounds obtained were characterized by nuclear magnetic resonance (NMR) (270-MHz) and their purity was tested by thin-layer chromatography (TLC) in the following solvents:

| | |
|---|---|
| $C_1$ = BuOH/AcOH/H$_2$O | 4:1:1 |
| $C_2$ = CHCl$_3$/MeOH | 7:3 |
| $C_3$ = CHCl$_3$/MeOH | 9:1 | or by high-performance liquid chromatography (HPLC)

EXAMPLE 1

L.TYR-D.SER-GLY-PHE-LEU-THR (XI)

This compound is prepared according to the following scheme:

| Tyr | D.Ser | Gly | Phe | Leu | Thr |
|---|---|---|---|---|---|
| | | Boc—OH | H—OCH$_3$ III | | |
| | | Boc— | —OCH$_3$ IV | | |
| Boc—OH I | H—OCH$_3$ Otbu | Boc— | —OH | H—OCH$_3$ | |
| Boc— II | —OCH$_3$ Otbu | Boc— V | —OCH$_3$ | | |
| Boc— | —OH Otbu | H— VI | —OCH$_3$ | | |
| Boc— | —Otbu VII | | —OCH$_3$ | | |
| Boc— | —Otbu VIII | | —OH | H—OCH$_3$ Otbu | |
| Boc— | —Otbu | | IX | —OCH$_3$ Otbu | |
| Boc— | —Otbu | | X | —OH Otbu | |
| H— | | | XI | —OH | |

N-BOC-L.TYROSYL-(OTBU)D.SERINE METHYL ESTER I 3.37 g Boc L. Tyr are added to 20 ml anhydrous THF. At 0° C. are successively added 2.54 g (Otbu)D-.Serinemethyl ester hydrochloride and 1.88 g NEt$_3$ dissolved in 20 ml anhydrous CHCl$_3$, followed by 1.84 g HOBT in 10 ml anhydrous CHCl$_3$ and, finally, 2.47 g DCC dissolved in 20 ml dry CHCl$_3$. The mixture is stirred for 1 hr at 0° C. and then for 12 hrs at room temperature. The DCU is filtered off, after which the material is evaporated to dryness in vacuo and taken up into 50 ml AcOEt. The insoluble DCU is filtered off. The resulting material is washed with 3×20 ml citric acid, 1×20 ml H$_2$O, 3×20 ml saturated NaHCO$_3$ solution, and then 2×20 ml H$_2$O. It is then dried over dry Na$_2$SO$_4$ and evaporated to dryness, to give a white product (4.68 g), Yield=89%. Rf=0.55 (C$_3$).

N-BOC-L.TYROSYL-(OTBU)D.SERINE II 2.19 g (5 mM) Boc Tyr-D.Ser(Otbu) methyl ester are dissolved in 10 ml methanol and stirred at 0° C. for 3 hrs with 10 ml 2 N NaOH. MeOH is evaporated off, water (10 ml) is added, the DCU is filtered off and the material is made acidic to pH2 with HCl. It is extracted with 3×30 ml AcOEt. The organic solvent is dried and evaporated to dryness, to give a white solid, Rf=0.52 (C$_2$).

BOC-GLYCYL-L.PHENYLALANINE METHYL ESTER III 5.25 g Boc Glycine are dissolved in 25 ml anhydrous THF at 0° C. Are then successively added 6.47 g L.Phe methylester in 20 ml dry CHCl$_3$, and 4.2 ml NEt$_3$ in 10 ml CHCl$_3$. After stirring for 10 minutes, 4.6 g HOBT in 20 ml THF are added thereto, followed by 6.19 g DCC dissolved in 50 ml CHCl$_3$. The material is stirred for 1 hr at 0° C. and then for 12 hrs at room temperature, after which it is treated as described for the production of compound I, to give 10 g of the desired product. Rf=0.45 (C$_3$).

BOC-GLYCYL-L.PHENYLALANINE IV 10 g of the preceding compound are dissolved in 60 ml MeOH. The material is stirred at 0° C. for 1 hr and then for 3 hrs at room temperature, after which it is treated as described for the production of Boc-Tyr-(Otbu)D.Ser, to give 7.2 g of a solid recrystallized from AcOEt.

BOC-GLY-L.PHE-L.-LEU METHYL ESTER V

The condensation reaction is effected as described for compound I, from 6.7 g tboc Gly-Phe OH and 3.81 g L.Leu methyl ester (hydrochloride), to give 7.64 g of a compound recrystallized from AcOEt. Rf=0.7 (C$_3$).

BOC-GLY-L.PHE-L.LEU-OCH$_3$ TRIFLUOROACETATE VI 4.64 g of compound V are dissolved in 15 ml TFA. The solution is stirred for 30 minutes at 0° C. and then for 30 minutes at room temperature. TFA is removed under high vacuum (0.1 mm Hg). The sirupy residue is stirred with 20 ml dry ether (10 times in succession) and the ether is filtered off. When the ether is neutral, the resulting white powder is rapidly suction filtered and then dried under high vacuum, to give 3.07 g of the desired material. Rf=0.5 (C$_2$).

BOC-TYR-(OTBU)D.SER-GLY-PHE-LEU-OCH₃ VII 1.69 g of compound II are dissolved in 15 ml dry THF. A solution of 1.85 g of compound VI and 0.56 ml NEt₃ in 15 ml CHCl₃ is added thereto. After 10 minutes, are successively added 0.61 g HOBT in 5 ml THF, followed by 0.82 g DCC in 5 ml CHCl₃. The mixture is stirred at 0° C. for 1 hr and then for 20 hrs at room temperature, after which it is treated as described in Example I, to give 1.75 g of a white solid. Yield=60%. Rf=0.65 (C₃).

BOC-TYR-(OTBU)D.SER-GLY-PHE-LEU-OH VIII 1.73 g of compound VII are stirred at 0° C. in 70 ml MeOH and 4.6 ml 1 N NaOH. After 1 hr at 0° C., the material is left at room temperature for 12 hrs, to give a white solid (1.33 g). Yield=80%. Rf=0.45 (C₂).

BOC-TYR-(OTBU)D.SER-GLY-PHE-LEU-(OTBU)THR-OCH₃ IX

The coupling reaction is effected between 1.33 g of compound VIII and 0.41 g L. Threonine methyl ester (HCl) under conditions similar to those used for the production of compound I or VII, to give 1.5 g of a white solid. Yield=90%. Rf=0.67 (C₃).

BOC-TYR-(OTBU)D.SER-GLY-PHE-LEU-(OTBU)THR-OH X

The saponification is effected with 1.5 g of compound IX and, using the procedure used for the production of compound VIII, gives 1.26 g of a white product Rf=0.8 (C₁).

H-TYR-D.SER-GLY-PHE-LEU-THR-OH XI 0.96 g of compound X are stirred for 30 minutes at 0° C. in 1 ml TFA saturated with gaseous HCl. The resulting material is then evaporated to dryness under 0,1 mm Hg. Dry ether is then added, and the material is triturated with 15×10 ml, to give 0.41 g of a creamy-white product. This is purified through a column of LH 20, using MeOH as solvent. The resulting white product is freeze-dried. Its purity is controlled by HPLC (Microbondapak C₁₈ column) Solvent: AcO⁽⁻⁾NH₄⁽⁺⁾. 10⁻²M, pH=4.2 (80%) and CH₃CN (20%). Rate of flow: 1.2 ml mn−1. Retention time: 10.2 mn.

EXAMPLE 2

TYR-D.ALA-GLY-PHE-LEU-THR XVIII

The compound is prepared according to the following scheme:

| Tyr | D.Ala | Gly | Phe | Leu | Thr |
|---|---|---|---|---|---|
| Boc—OH | H—OCH₃ | Boc—————XIII————OH | | | OCH₃ Otbu |
| | | | Boc——XIV——OCH₃ Otbu | | |
| Boc—————XII————OCH₃ | | Boc———XV———OCH₃ Otbu | | | |
| Boc———————OH | H——————XVI——————OCH₃ Otbu | | | | |
| Boc—————————————XVII—————————————OCH₃ Otbu | | | | | |
| Boc—————————————XVIII—————————————OCH₃ | | | | | |
| H————————————————————————————————OH | | | | | |

BOC-TYR-D.ALA METHYL ESTER XII

The above material is obtained by condensation of 4.2 g Boc Tyr with 1.74 g D. alanine methyl ester hydrochloride under the conditions described for the production of compound I, to give a solid material which is saponified with 1 N sodium hydroxide, thus obtaining 3.92 g of compound XII. Rf=0.51 (C₂).

BOC-GLY-PHE-LEU XIII

Compound XIII is obtained as disclosed for the production of compound IV, from 6.4 g of compound V, to give 5.2 g of material recrystallized from AcOEt. Rf=0.48 (C₃).

BOC-GLY-PHE-LEU-(OTBU)THR-OCH₃ XIV

This compound is obtained in the same manner as compound VIII, by condensation of 5.2 g of compound XIII with 1.70 g (Otbu)threonine methyl ester hydrochloride, to give a pale yellow solid (3.27 g). Rf=0.61 (C₃).

GLY-PHE-LEU-(Otbu)THR-OCH₃ XV

Compound XIV is stirred in TFA (1.8 ml) at 0° C. for 1 hr, and is then treated under the same conditions used for the production of compound VI.

The remaining part of the synthesis is then effected via the methods illustrated in Example 1.

The ultimate compound, XVIII, is a white solid, Rf=0.33 (C₁).

Following Table I gives the formulae of compounds of the general formula (I) prepared according to the procedures used in the preceding Examples or according to modifications of conventional techniques used in peptide synthesis.

TABLE I

| N° | FORMULA | Rf |
|---|---|---|
| 1 | Tyr—D.Ser—Gly—Phe—Leu—Thr | 0.51 (C₁) |
| 2 | Tyr—D.Ala—Gly—Phe—Leu—Thr | 0.33 (C₁) |
| 3 | Tyr—D.Ser—Gly—Phe—Leu—Ser | 0.62 (C₁) |
| 4 | Tyr—D.Thr—Gly—Phe—Leu—Ser | 0.58 (C₁) |
| 5 | Tyr—Aib—Gly—Phe—Leu—Ser | 0.35 (C₁) |
| 6 | Tyr—AzaGly—Gly—Phe—Leu—Ser | 0.44 (C₁) |
| 7 | Tyr—Aib—Gly—Phe—Leu—Thr | 0.57 (C₁) |
| 8 | Tyr—AzaGly—Gly—Phe—Leu—Thr | 0.40 (C₁) |
| 9 | Tyr—D.Ser—Gly—Phe—Leu—NH(CH₂)₂OH | 0.30 (C₁) |
| 10 | Tyr—D.Ser—Gly—Phe—Leu—NH(CH₂)₃OH | 0.30 (C₁) |
| 11 | Tyr—D.Ser—Gly—Phe—Leu—Thr NH₂ | 0.12 (C₁) |
| 12 | Tyr—D.Ser(Obenzyl)—Gly—Phe—Leu—Thr | 0.50 (C₂) |
| 13 | Tyr—D.Ser(Obenzyl)—Gly—Phe—Leu—Thr(Obenzyl) | 0.47 (C₃) |

TABLE I-continued

| N° | FORMULA | Rf |
|---|---|---|
| 14 | Tyr—D.Ser—Gly—Phe—Leu—Thr OMe | 0.30 (C$_2$) |
| 15 | Tyr—D.Ser(Obenzyl)—Gly—Phe—Leu—Thr OMe | 0.52 (C$_3$) |
| 16 | Tyr—D.Ser(Op.fluorobenzyl)—Gly—Phe—Leu—Thr. O hexa fluorobenzyl | 0.61 (C$_3$) |
| 17 | Tyr—D.Ser—Gly—p.F.Phe—Leu—Thr | 0.57 (C$_1$) |
| 18 | Tyr—AzaGly—Gly—Phe—p.F.—Leu—Thr | 0.46 (C$_1$) |
| 19 | Tyr—AzaGly—Gly—Phe—Leu—Thr—O hexafluorobenzyl | 0.80 (C$_2$) |
| 20 | Tyr—D.Ser(OCO p.fluorophenyl)—Gly—Phe—Leu—Thr—Obenzyl | 0.75 (C$_3$) |
| 21 | Tyr—D.Ser(OCO p.fluorophenyl)—Gly—Phe—Leu—Thr(OCO p.fluorophenyl)O—benzyl | 0.81 (C$_3$) |
| 22 | Tyr—Aib—Gly—Phe—Leu—Thr—O hexafluorobenzyl | 0.50 (C$_2$) |
| 23 | Tyr—Aib—Gly—penta fluoro Phe—Leu—Thr—O hexafluorobenzyl | 0.55 (C$_2$) |
| 24 | Tyr—D.Ser(OCO p.fluorobenzyl)—Gly—p.F.Phe—Leu—Thr—OMe | 0.48 (C$_3$) |
| 25 | Tyr—D.Ser—Gly—Phe—N.Leu—Thr | 0.50 (C$_1$) |
| 26 | Tyr—D.Ser—Gly—Phe—Ile—Thr | 0.50 (C$_1$) |
| 27 | Tyr—D.Ser—Gly—Phe—Ile—Ser | 0.58 (C$_1$) |
| 28 | Tyr—D.Ser—(OCO p.fluorobenzyl)—Gly—Phe—Leu—Ser—O hexafluorobenzyl | 0.75 (C$_3$) |
| 29 | Tyr—D.Ser (OCOCH$_3$)—Gly—Phe—Leu—Ser (OCOCH$_3$) O hexafluorobenzyl | 0.70 (C$_3$) |
| 30 | Tyr—D.Ser—Gly—Phe—Leu—NH(CH$_2$)$_2$—OCO hexafluorobenzyl | ND |
| 31 | Tyr—D.Ser(OCOCH$_3$)—Gly—Phe—Leu—Thr—O hexafluorobenzyl | ND |
| 32 | Tyr—D.Cys—Gly—Phe—Leu—Thr | 0.25 (C$_1$) |
| 33 | Tyr—D.Cys(SCOC$_6$H$_5$)—Gly—Phe—Leu—Thr—Ohexafluorobenzyl | ND |
| 34 | Tyr—D.Ser—Gly—Phe—Leu—Thr—NH—CH$_2$—C$_6$H$_5$ | 0.40 (C$_1$) |
| 35 | Tyr—D.Ser—Gly—Phe—Leu—Thr—NH—CH$_2$—C$_6$F$_5$ | ND |
| 36 | Tyr—D.Ser(OCO p.fluorophenyl)Gly—Phe—Leu—Thr—NHCH$_2$C$_6$F$_5$ | 0.62 (C$_3$) |
| 37 | Tyr—D.Ser—Gly—Phe—Leu—Thr—NH—phosphatidylethanolamine | ND |
| 38 | Tyr—βPhe.Ser—Gly—Phe—Leu—Thr | ND |
| 39 | Tyr—βOH Leu—Gly—Phe—Leu—Thr | ND |
| 40 | Tyr—4 OH Ile—Gly—Phe—Leu—Thr | ND |
| 41 | Tyr—αOH Nor Val—Gly—Phe—Leu—Thr | ND |
| 42 | Tyr—βOH Nor Val—Gly—Phe—Leu—Thr | ND |
| 43 | Tyr—αOH Nor Val—Gly—Phe—Leu—Thr. | ND |
| 44 | Tyr—D.Ser—Gly—Phe—Leu—Thr—NH(CH$_2$)$_2$N(↑O)—(CH$_3$)$_2$ | 0.50 (C$_2$) |
| 45 | Tyr—D.Ser—Gly—Phe—D.Leu | |
| 46 | Tyr—D.Thr—Gly—Phe—D.Leu | |
| 47 | Tyr—D.Ser—Gly—p.F.Phe—D.Leu—O—benzyl | |
| 48 | Tyr—D.Ser—Gly—p.F.Phe—D.Leu—O—benzyl | |

In Table I, the groups between parentheses correspond to substituents attached to the side-chains.

As formerly indicated, the compounds of the formula (I) possess particularly valuable pharmacological properties, and most particularly a preferential action on σ opiate receptors, together with an analgesic and a psychotropic action. Their toxicity appears only at dosages highly superior to the pharmacologically active dosages, which makes them therapeutically useful, typically as analgesic, psychotropic and anti-diarrheic agents.

Results of pharmacological and toxicological investigations which demonstrate said properties are given below.

1-In Vitro Action on μ and σ Receptors

The study of the action on μ receptors or on σ receptors was conducted as a function of the effect on the isolated ileum of guinea-pigs or on the vas deferens of mice.

The action on the μ receptors was determined by the measure of the 50% inhibiting concentration (IC 50) of the contraction of the isolated ileum of guinea-pigs, induced by coaxial stimulation (PATON W.D.M., Brit.J. Pharm. 1959, 12, 119).

The action on the σ receptors was determined by the measure of the 50% inhibiting concentration (IC 50) of the contraction of the vas deferens of mice, induced by electric stimulation.

The 50% inhibiting concentrations are expressed as nanomolar/liter concentrations. Each product is tested with respect to Met-Enkephalin as reference material and the results obtained are also expressed as % activity with respect to Met-Enkephalin = 100.

The ratio $$R = \frac{IC\ 50\ ileum}{IC\ 50\ vas\ deferens}$$

makes it possible to find out whether the test material is 82- or σ- specific. The results obtained are set forth in the following Table. In said Table, the number of experiments is indicated between parentheses.

TABLE II

| PRODUCT | ILEUM IC 50 (nM) | ILEUM Relative action | VAS DEFERENS IC 50 (nM) | VAS DEFERENS Relative action | R IC 50 ileum IC 50 V.D. |
|---|---|---|---|---|---|
| Met-Enkephalin | 354 (6) | 100 | 18 (4) | 100 | 19.6 |
| Example 1 | 637 (5) | 55 | 0.80 (5) | 2250 | 796 |
| Example 2 | 500 (3) | 80 | 2 (2) | 900 | 250 |
| Example 25 | 1050 (2) | 34 | 1.2 (2) | 1500 | 875 |
| Example 45 | 247 (4) | 143 | 1.15 (4) | 1565 | 215 |
| Example 13 of patent FR 78 12 543⊕ | 320 | 110 | 650 | 2.7 | 0.49 |

⊕Compound of the formula:
Tyr—D.Ala—Gly—Phe—Met—NH—(CH$_2$)$_5$—SO$_2$NH

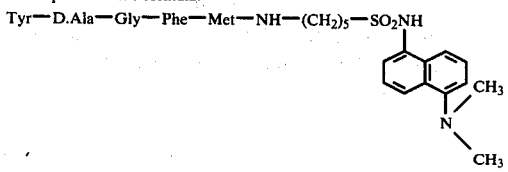

The σ-specific effect of the compounds of the formula (I) is apparent from the results set forth in Table II.

2-Analgesic Activity

The compounds were tested in vivo by the intravenous route (i.v.) in mice, using the hot-plate (65° C.) test in mice, according to the method disclosed by JACOB & BLOZOVSKI (Arch.Int.Pharmacodyn. 1961, 33,296) by determination of the licking reflex at 15 minutes, of the leap at 30 minutes and of the adjusted jump at 60 and 90 minutes.

DAla$_2$Met-Enkephalin was used as reference material.

The results obtained are set forth in Table III.

3-Naxolone Susceptibility Test-Determination of the Appearance of Dependence This test makes it possible to evaluate the dependence induced by chronic administration of morphinic analgesics. It comprises inducing the dependence condition after 10 days of treatment by injection of a high doage of an antagonist: naxolone. Compound 1 was tested by ICV administration in rats, using the technique according to Frederickson et al., Res. Common.Pathol.Pharmacol. 5, 867(1973).

TABLE III

| Treatment | N | 15' Licking | 30' Leap | 60' Adjusted jump | 90' Adjusted jump |
|---|---|---|---|---|---|
| i.v. Controls | 6 | 4.5 ± 0.8 | 2.9 ± 2.2 | 13.4 ± 6.6 | 13.4 ± 5.3 |
| D.Ala$_2$Met-Enkephalin 100 mg/kg i.v. | 6 | 5.5 ± 1 | 5.5 ± 1.6 | 5.5 ± 1.2 | 5.6 ± 2 |
| Ex. 1 35 mg/kg i.v. | 6 | 29.4 ± 3.2 | 30.1 ± 5.7 | 28.6 ± 7.2 | 32.2 ± 9.2 |
| Ex. 2 100 mg/kg i.v. | 6 | 38.2$^x$ ± 4.5 | 35.7$^x$ ± 6.4 | 34.9$^x$ ± 5.1 | 29.8$^x$ ± 2.6 |
| Ex. 25 75 mg/kg i.v. | 6 | 37.4$^x$ ± 1.6 | 34.6$^x$ ± 6.3 | 35.4$^x$ ± 8 | 30.4$^x$ ± 9 |

$^x$p < 0.05

The results obtained are set forth in Table IV below and are compared with those obtained with morphine.

TABLE IV

| Treatment | N | Naxolone | Abstinence test (jumps) |
|---|---|---|---|
| ICV controls (saline solution) | 5 | 10 mg/kg s.c. on the 10th day | 12 ± 3 |
| Compound I 25 mg/kg 4 times a day for 10 days | 5 | 10 mg/kg s.c. on the 10th day | 10 ± 2 |
| Morphin 25 mg/kg 4 times a day for 10 days | 5 | 10/mg/kg s.c. on the 10th day | 74 ± 11 |

4-Anti-Diarrhea Action

This action was investigated by the castor oil test in rats, using the method according to Niemegeers and co-workers (Arzn.-Forsch. 22, 516–518, 1972).

The tests were conducted with male rats of 160–220 g body weight. After an 18 hr fasting period, each animal was orally administered 1 ml castor oil.

The test compounds, dissolved in water, were administered orally under a volume of 0.5 ml per 100 g body weight, one hour prior to the castor oil administration.

The results obtained are set forth in following Table V.

TABLE V

| Series | Number of rats | Number of non-diarrheic animals 2 hours | Number of non-diarrheic animals 4 hours |
|---|---|---|---|
| Control$^x$ | 30 | 8 | 2 |
| Example 25 3 mg/kg | 10 | 10 | 6 |
| Codein base 3 mg/kg | 10 | 7 | 4 |
| 10 mg/kg | 10 | 10 | 7 |
| Morphin (hydrochloride) 1 mg/kg | 10 | 9 | 4 |
| 3 mg/kg | 10 | 10 | 6 |

$^x$Castor oil alone

5-Action of the Claimed δ-Specific Compounds on the Metabolism of Dopamine Which is Characteristic of the Psychotropic Activity Under Consideration The selective action of compound I on the liberation of dopamine is demonstrated by ICV injection tests of morphine, of DAla$^2$Met.Enkamide and of compound I (Chenelet et al., Nature (1981) 291, 320).

Spontaneous liberation of dopamine is increased by a factor of 50% by morphin ($10^{-6}$M), and by a factor of 100% by DAla$^2$Met.Enkamide ($10^{-6}$M), and by 100% also by compound I at a dosage ($5 \times 10^{-8}$M) 20 times lower than the preceding peptide which exhibits but a low preference for δ receptors.

This preferential effect of δ-specific compound I on the dopaminergic receptors may be evidenced by i.v.

administration of compound I and determination of the locomotor activity according to STINUS et al. Proc.-Natl. Acad.Sci.USA 77, 2302 (1980). The results obtained are set forth in Table VI. Each experiment was conducted on a group of 10 animals (male rats weighing 200–250 g) and the results obtained were compared with those of a reference group.

TABLE VI

| Compounds | Locomotor activity |
|---|---|
| Saline phys. sol. | $100 \pm 15\%$ |
| Compound I (5 mg/kg) | $65 \pm 10\%$ |

6-Acute Toxicity

Death rate determination in mice is effected after a single intravenous administration of increasing dosages of the test compounds.

$LD_{50}$ for all compounds of the formula (I) tested is in excess of 300 mg/kg i.v.

The therapeutic composition of this invention is administrable to humans orally, as tablets, coated tablets, capsules, drops or syrups. For rectal administration, it may also be formulated as suppositories and, for parenteral administration, as injectable solutions.

Each unit dose contains advantageously 0.2–100 mg active ingredient, thus:
for tablets: 0.2–30 mg active ingredient
for suppositories: 10–50 mg active ingredient
for injectable ampoules (1 ml): a solution containing 0.5–2% active ingredient in a sterile physiologic solution.

The daily dosage regimen may vary from about 5 mg to about 200 mg active ingredient.

The therapeutic composition of this invention is administrable to humans for the treatment of pain or diarrhea.

In view of its psychotropic activity, it is also applicable to the treatment of psychoses and neuroses.

For illustrative purposes, tablets containing 10 mg active ingredient may be formulated as follows:

| Compound I | 10 mg |
|---|---|
| Corn starch | 100 mg |
| Lactose | 380 mg |
| Gelatin | 4 mg |
| Magnesium stearate | 6 mg |
| Finished tablet | 500 mg. |

We claim:
1. Peptide derivatives having the formula

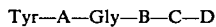
Tyr—A—Gly—B—C—D    (I)

in which:
A is a D.Ser, D.Thr, D.Cys, homo Serine, βPhe Ser, βOH Leu, 4OH Ile, α,β,γ OHNor Val or OH Val residue in which the side-chain OH or SH groups may be free or protected by (i) a straight-or branched-chain alkyl radical having 1–6 carbon atoms, (ii) an unsubstituted phenyl radical or a phenyl radical substituted with one or more fluorine atoms, (iii) an unsubstituted benzyl radical or a benzyl radical substituted with one or more fluorine atoms, (iv) an aliphatic acyl radical having 1–6 carbon atoms or an acyl radical of the formula COX in which X is a phenyl, benzyl or benzhydryl radical, optionally substituted with one or more fluorine atoms, B is a L.Phe, pF.L.Phe or pentafluoro L.Phe residue,
C is a Leu, N.Leu or Ile residue having D or L configuration,
D represents a group of the formula:

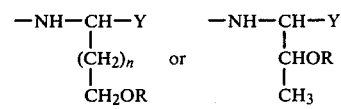

in which n=0, 1 or 2,
R is a hydrogen atom or a radical as defined for the protection of the OH group of residue A,
Y is a hydrogen atom, a hydroxy, carboxy, carbamoyl oxy group, a group $OR_1$, $COOR_1$ or $CONHR_1$ in which $R_1$ represents a radical such as defined for the protection of the OH group of residue A, a phosphatidylethanolamine chain, or a chain

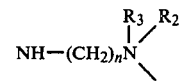

in which n is an integer from 0 to 3, $R_2$ is a hydrogen atom or a straight alkyl radical containing 1–4 carbon atoms, and $R_3$ is a hydrogen or oxygen atom or a straight alkyl residue having 1–4 carbon atoms
and their pharmaceutically acceptable salts.

2. Peptide derivatives having the general formula:

Tyr—A—Gly—B—C—D    (I)

in which:
A is a D.Ser, D.Thr, D.Cys, βPhe Ser, αOH Leu, 4OH Ile or α,β,γ OHNor Val residue in which the side-chain OH or SH groups may be free or protected by (i) an unsubstituted benzyl radical or a benzyl radical substituted with one or more fluorine atoms, (ii) an aliphatic acyl radical having 1–6 carbon atoms or
an acyl radical of the formula COX in which X is a phenyl, benzyl or benzhydryl radical, optionally substituted with one or more fluorine atoms, B is a L.Phe, pF.L.Phe or pentafluoro L.Phe residue,
C is a Leu, N.Leu or Ile residue having D or L configuration,
D represents a group of the formula:

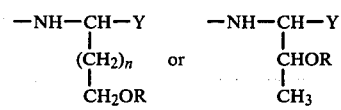

in which n=0 or 1,
R is a hydrogen atom or a radical as defined for the protection of the OH group of residue A,
Y is a hydrogen atom, a carboxy, carbamoyl oxy group, a group $COOR_1$ or $CONHR_1$ in which $R_1$ represents an alkyl radical having 1–4 carbon atoms or a radical such as defined for the protection of the OH group of residue A, a phosphatidylethanolamine chain, or a chain

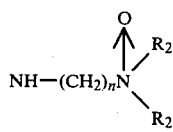

in which n is an integer from 0 to 3 and $R_2$ is a straight alkyl radical containing 1–4 carbon atoms, and their pharmaceutically acceptable salts.

3. Peptide having the formula: Tyr-D.Ser-Gly-Phe-Leu-Thr.

4. Peptide having the formula: Tyr-D.Ser-Gly-Phe-N.Leu-Thr.

5. Therapeutic composition having in particular analgesic, psychotropic and anti-diarrheic activities, comprising, as active ingredient, an effective amount of a peptide derivative having the formula:

Tyr—A—Gly—B—C—D  (I)

in which:

A is a D.Ser, D.Thr, D.Cys, homo Serine, βPhe Ser, βOH Leu, 4OH Ile, α,β,γ OHNor Val or OH Val residue in which the side-chain OH or SH groups may be free or protected by (i) a straight-or branched-chain alkyl radical having 1–6 carbon atoms, (ii) an unsubstituted phenyl radical or a phenyl radical substituted with one or more fluorine atoms, (iii) an unsubstituted benzyl radical or a benzyl radical substituted with one or more fluorine atoms, (iv) an aliphatic acyl radical having 1–6 carbon atoms or an acyl radical of the formula COX in which X is a phenyl, benzyl or benzhydryl radical, optionally substituted with one or more fluorine atoms, B is a L.Phe, pF.L.Phe or pentafluoro L.Phe residue, C is a Leu, N.Leu or Ile residue having D or L configuration, D represents a group of the formula:

in which n=0, 1 or 2,

R is a hydrogen atom or a radical as defined for the protection of the OH group of residue A, Y is a hydrogen atom, a hydroxy, carboxy, carbamoyl oxy group, a group $OR_1$, $COOR_1$ or $CONHR_1$ in which $R_1$ represents a radical such as defined for the protection of the OH group of residue A, a phosphatidylethanolamine chain, or a chain

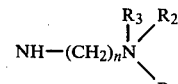

in which n is an integer from 0 to 3, $R_2$ is a hydrogen atom or a straight alkyl radical containing 1–4 carbon atoms, and $R_3$ is a hydrogen or oxygen atom or a straight alkyl residue having 1–4 carbon atoms and its pharmaceutically acceptable salts.

* * * * *